United States Patent [19]

Tiffany et al.

[11] 4,226,531
[45] Oct. 7, 1980

[54] DISPOSABLE MULTI-CUVETTE ROTOR

[75] Inventors: Thomas O. Tiffany; Gilbert B. Manning, both of Spokane; Philip C. Thayer, Nine Mile Falls; Chris M. Coelho, Veradale, all of Wash.

[73] Assignee: Instrumentation Laboratory Inc., Lexington, Mass.

[21] Appl. No.: 828,609

[22] Filed: Aug. 29, 1977

[51] Int. Cl.³ .............................................. G01N 1/10
[52] U.S. Cl. .............................. 356/246; 250/576; 422/258
[58] Field of Search ............... 356/197, 246, 244, 427, 356/440; 250/576; 233/26, 27; 422/258, 72; 307/10 R

[56] References Cited

U.S. PATENT DOCUMENTS

| | | | |
|---|---|---|---|
| 2,456,743 | 12/1948 | Short | 307/10 R |
| 3,547,547 | 12/1970 | Anderson | 356/427 |
| 3,555,284 | 1/1971 | Anderson | 356/246 X |
| 3,565,537 | 2/1971 | Fielding | 356/246 |
| 3,582,218 | 1/1971 | Anderson | 356/246 X |
| 3,586,484 | 6/1971 | Anderson | 250/576 X |
| 3,744,975 | 7/1973 | Mailen | 422/72 |
| 3,759,666 | 9/1973 | Hill, Jr. | 233/26 |
| 3,798,459 | 3/1974 | Anderson et al. | 250/218 |
| 3,800,161 | 3/1974 | Scott et al. | 250/564 |
| 3,813,031 | 5/1974 | Anderson | 233/26 |
| 3,829,223 | 8/1974 | Hamel | 356/246 |
| 3,873,217 | 3/1975 | Anderson et al. | 356/197 X |
| 3,899,296 | 8/1975 | Mailen et al. | 422/72 X |
| 4,088,448 | 5/1978 | Lilja et al. | 356/246 X |
| 4,123,173 | 10/1978 | Bullock et al. | 356/197 X |

OTHER PUBLICATIONS

Tiffany et al., "A Propagation of Error Analysis of the Enzyme Activity Expression, A Model for Determining the Total System Random Error of a Kinetic Enzyme Analyzer," *Clinical Chemistry*," vol. 22, No. 9, (Sep. 1976), p. 1438.
Burtis et al., "Development of a Miniature Fast Analyzer," vol. 18, No. 8, (Aug. 1972), p. 753.

*Primary Examiner*—John K. Corbin
*Assistant Examiner*—Bruce Young Arnold

[57] ABSTRACT

A disposable multi-cuvette rotor for use in an analytical photometer which comprises two injection molded parts from a transparent material of suitable chemical and absorption characteristics. These parts are joined together by ultrasonic welding and when so joined, define a plurality of radially-arranged cuvettes being separated by triangularly-shaped open spaces. Each of the cuvettes is divided into adjoining sample and reagent/measuring chambers by a wedge-shaped dam in a manner that the chambers are communicating with one another through an open space above the dam. There are pairs of recessed optical windows formed in both of the parts which are axially aligned and positioned adjacent the chambers of the greater radial distance so as to provide opposing planar walls defining an optical path through the chambers. There is provided a further integral optical window in the radial outer wall of each reagent/measuring chamber for use of the chamber in a light scattering or fluorescent measuring mode. A plurality of loading ports are provided in the cover portion in two concentric rings in a manner that each loading port communicates with each one of the chambers of the cuvettes whereby discrete portions of samples and reagents may be respectively loaded into the adjoining chambers separated by the wedge-shaped dams.

8 Claims, 7 Drawing Figures

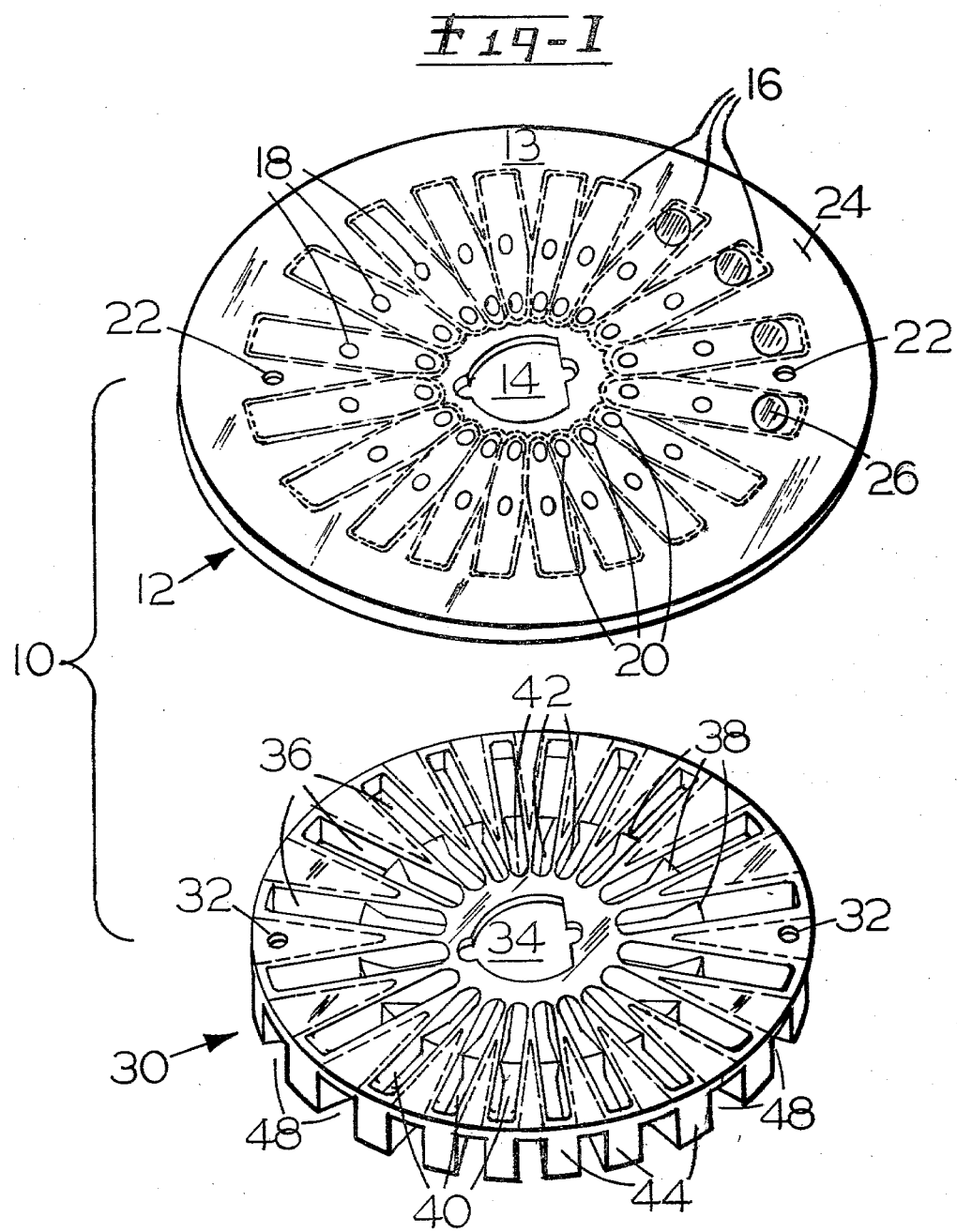

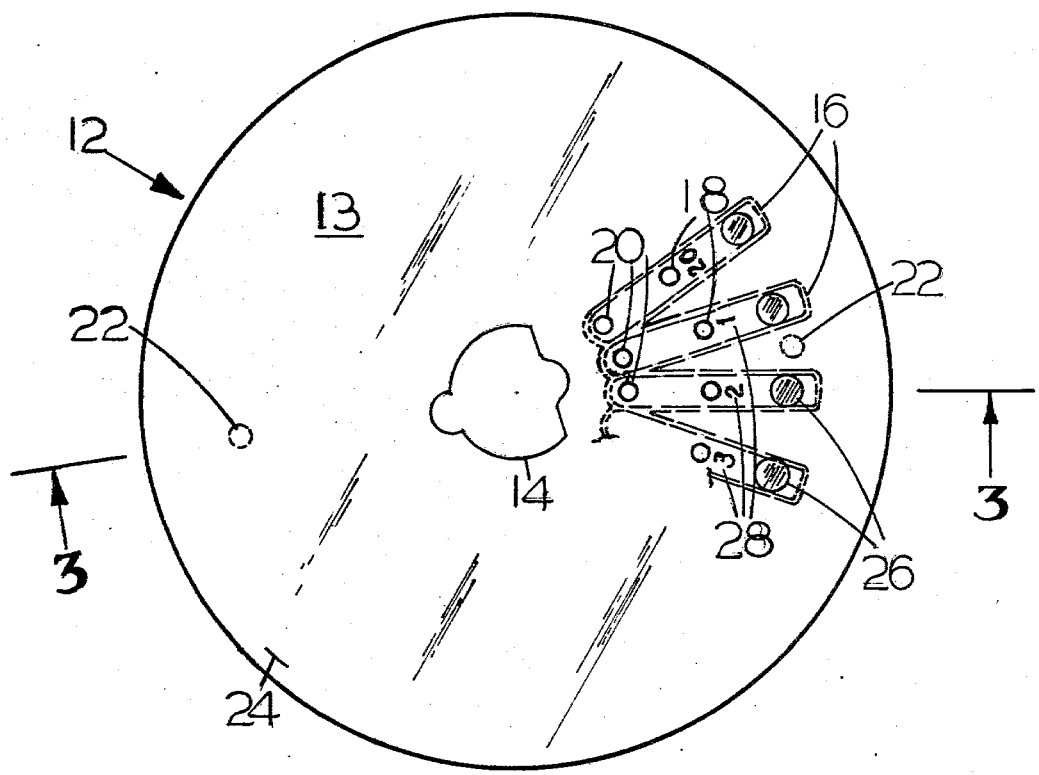
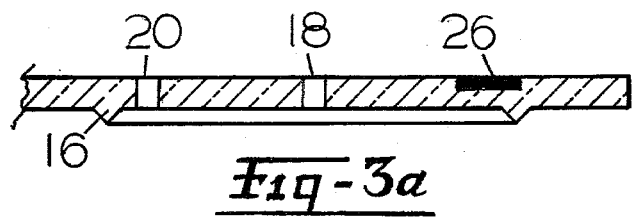
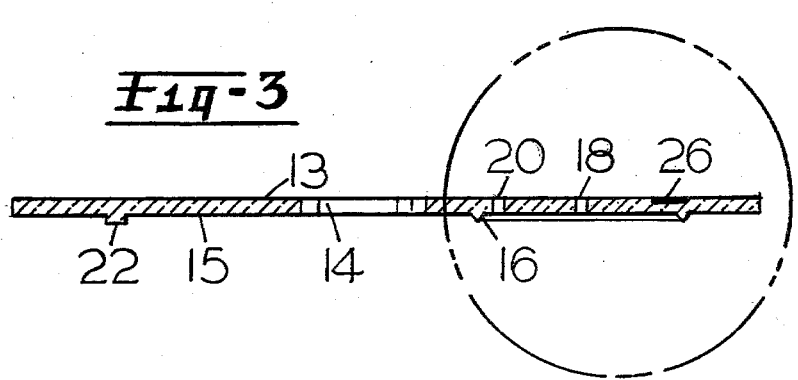

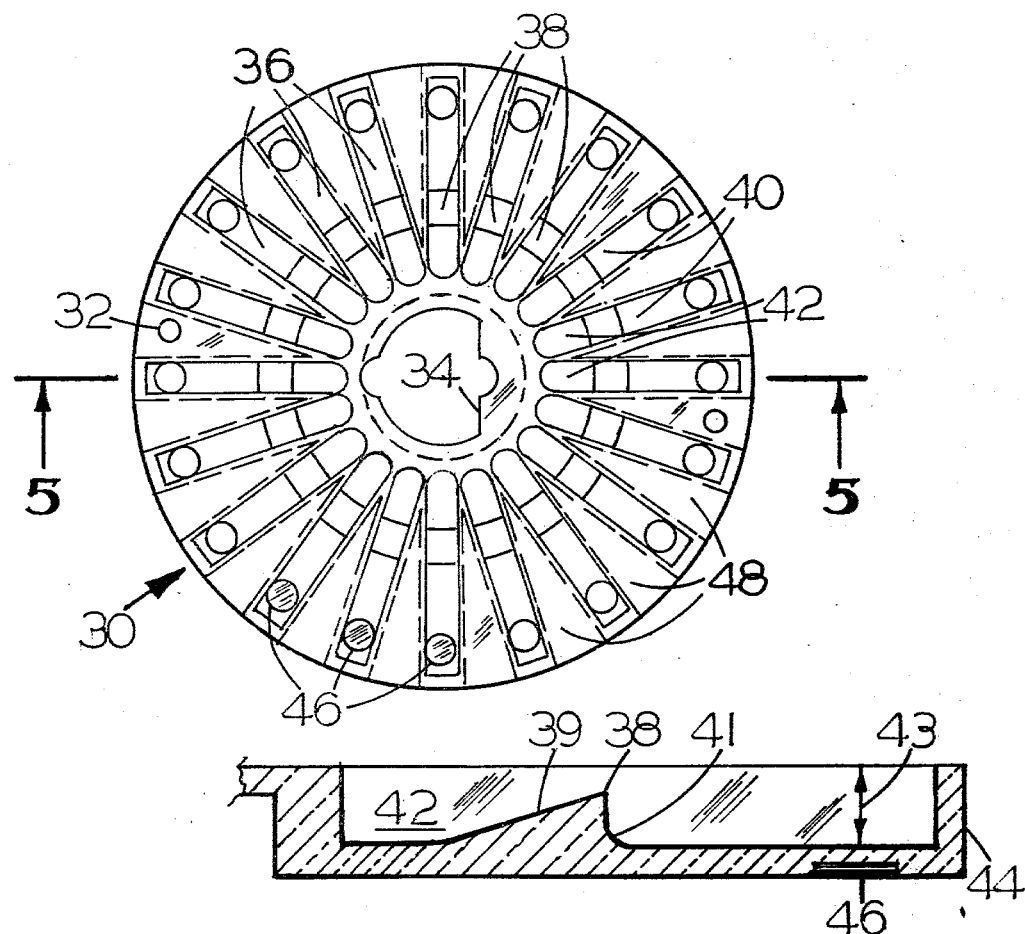
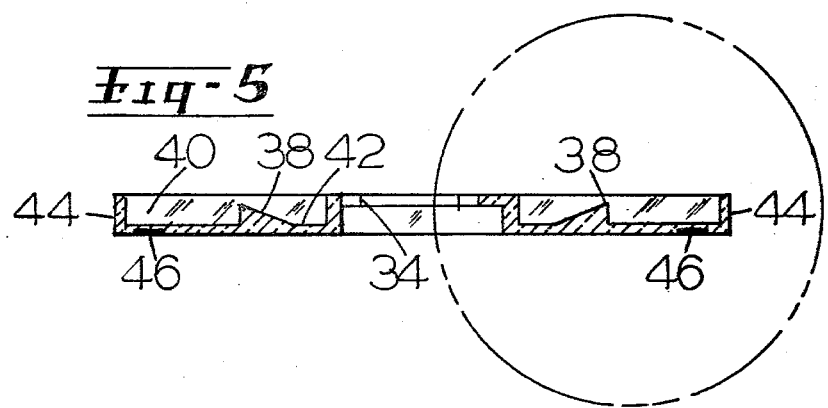

DISPOSABLE MULTI-CUVETTE ROTOR

BACKGROUND OF THE INVENTION

The invention described herein relates generally to disposable cuvette rotors and more particularly to an improved disposable multi-cuvette rotor which can be conveniently injection molded of two parts and joined together by ultrasonic welding, and because of its uniquely shaped configuration, exhibits advantages over cuvettes heretofore known and allows their greater utilization at reduced cost.

Such disposable cuvette rotors find operational use in a miniature fast photometric analyzer of the type more specifically described in an article entitled "Development of a Miniature Fast Analyzer," Clinical Chemistry, Vol. 18, No. 8, August 1972. In such analyzers, centrifugal force is used to transfer and mix samples and reagents previously loaded into a multi-cuvette rotor by rotating the same. A stationary photometer scans the cuvettes during rotation and generates a multiplicity of signals representative of the reactions taking place in each of the cuvettes following the mixture therein of the samples with the reagents. The signals thus generated are evaluated by a computer which allows the reactions taking place to be observed as they occur. These analyses are fast, reliable and substantially error free because all chemical reactions are initiated simultaneously at the time of their transfer and mixing, and are coupled with the continuous referencing of the spectrophotometric system of the analyzer; thus errors due to electronic, mechanical, or chemical drift are minimized, if not eliminated.

One of the limiting factors in the commercialization of such fast analyzers has been the multi-cuvette rotor. Most cuvette rotors have been relatively large and of complex structure, normally comprising three or more parts and, secured together by various means such as by being bolted together or fastened to one another by adhesives, glues, or the like. Such rotors have been expensive to manufacture and to use and, because of their cost, they were undesirable. The rotors also had to be cleaned thoroughly and entirely in between analytical runs in order to avoid contamination of subsequent samples.

A need therefore has existed for a disposable relatively low-cost multi-cuvette rotor that will be both inexpensive to manufacture and inexpensive and convenient to use in such a fast photometric analyzer. Accordingly, it is an object of the present invention to provide a disposable low-cost multicuvette rotor for use in a miniature fast spectrophotometric analyzer. More specifically, it is an object of the invention to provide such a disposable multi-cuvette rotor that may be conveniently injection molded of two parts from a transparent material of suitable chemical and absorption characteristics, which parts may thereafter be conveniently joined to one another by ultrasonic welding techniques.

Other objects of the invention will become more fully apparent upon examination of the following description in light of the appended drawings.

PRIOR ART

A representative analytical photometer of the rotary cuvette type and its method of use are described in U.S. Pat. No. 3,555,284 granted Jan. 12, 1971. The rotary cuvette shown and described in that patent, note particularly FIG. 2 thereof, is a relatively large and complex structure made of glass and polytetrafluorethelene rings sandwiched together and secured between a steel rotor body and a bolted flange ring. Such rotors are very expensive to manufacture and, in addition, must be thoroughly cleaned between different sample runs so as to avoid cross contamination.

What is believed to have represented the next stage in the development of such a rotor is described in the article in *Clinical Chemistry* mentioned above. The same rotary cuvette is also and more fully described in U.S. Pat. No. 3,798,459 granted Mar. 19, 1974, note particularly FIGS. 3 and 4 thereof. The rotor shown is of a laminated design with a central, preferably opaque plastic disc sandwiched between outer transparent discs. A circular array of axially extending apertures are provided in this central disc to serve as sample analysis cuvettes. These rotor discs are machined and then assembled by gluing them together with a low viscosity epoxy glue.

A more complex rotary cuvette is described in U.S. Pat. No. 3,547,547 patented Dec. 15, 1970 in which air pressure and/or vacuum is used to effect liquid transfer between the cavities. A different kind of rotary cuvette is described in U.S. Pat. No. 3,582,218 granted June 1, 1971. Here the rotor is adapted to carry a plurality of removable individual cuvettes in the form of rigid hollow elongated bodies exteriorly engaged by a flange seating against an axially extending surface of the rotor. These individual cuvettes may be affixed to a flexible belt to facilitate their transport, installation, and removal in unison.

Another rather complicated rotary cuvette is disclosed in U.S. Pat. No. 3,586,484 granted June 22, 1971 wherein a central transfer disc is shown, among others, with three series of chambers. A further variation of still another complex rotary cuvette is shown and described in U.S. Pat. No. 3,744,975 granted July 10, 1973. The rotor here again comprises a laminated member with a central opaque disc sandwiched between outer transparent discs. Finally, U.S. Pat. No. 3,800,161 granted Mar. 26, 1974 discloses a portable dynamic multi-station analyzer that may be used both in a photometric mode and in a fluorometric measurement mode.

SUMMARY OF THE INVENTION

In accordance with the present invention, a disposable multi-cuvette rotor for use in an analytical photometer is provided which is relatively inexpensive and simple to manufacture and, which nevertheless incorporates unique features so as to enhance its usefulness and reduces both the time and expense of its utilization in running tests through the analyzer.

More specifically, the disposable multi-cuvette rotor is conveniently injection molded of only two parts from a transparent material of suitable chemical and absorption characteristics selected from the group of ultraviolet transmitting acrylics, polyolefins, styrenes, polycarbonates, combinations of butadiene and/or acrylonitrile with styrene, cellulosics, polyamides and polyester resins. These two injection molded parts are then joined together by ultrasonic welding techniques and when so joined, define a plurality of radially arranged cuvettes in a manner that each of the cuvettes is separated one from the other by triangularly-shaped open spaces such as flutes or chutes. The significance of this fluted design resides in that a much greater surface area of each cuvette, namely three sides thereof, is available to facilitate maximum and rapid heat transfer throughout the rotor and through each cuvette. Consequently, both the samples and reagents admitted into the cuvettes can be brought to temperature equilibrium at a more rapid rate than has heretofore been possible.

Wedge-shaped dams having inclined surfaces increasing radially outward until they reach about half the depth of these cuvettes followed by adjoining vertical and slightly arcuate surfaces divide each of the cuvettes into adjoining and communicating sample and reagent-/measuring chambers in a manner that, at rest or at low rotational speeds, the two substances, deposited through different loading ports on each side of said dams, are kept separate from one another. However, at increased rotational speeds, the samples are transferred by centrifugal forces over these dams to mix with the reagents in the measuring chambers.

Recessed optical windows of the proper optical surface finish are furthermore provided for each cuvette so as to form opposed planar walls defining an axially aligned optical path through each of the measuring chambers of the cuvettes. These windows are recessed to protect their optical finish during handling. Since the rotor is also designed for fluorometric measurements, the radial ends of the cuvettes have also been given an optical surface finish of the required type. In order to protect these end optical windows during the handling of the rotors, the cover member of the rotor is formed with a diameter larger than that of the diameter of the body member. The resultant disposable multi-cuvette rotor of the invention may be used either in an absorbent measuring mode or in a fluorometric measuring mode. The rotor of the invention is conveniently formed with a substantially "D"-shaped central opening so as to facilitate its convenient and secure location with respect to a simlarly "D"-shaped support member provided in the miniature fast analyzer with which it is used.

BRIEF DESCRIPTION OF THE DRAWINGS

FIG. 1 is an exploded perspective view of the two members comprising the disposable multi-cuvette rotor made in accordance with the invention;

FIG. 2 is a plan view of one of the members, namely the cover member of the multi-cuvette rotor shown in FIG. 1;

FIG. 3 is a section through the cover member along the line shown by the arrows 3—3;

FIG. 3a represents a portion on an enlarged scale of the cover member shown in FIG. 3;

FIG. 4 is a plan view of the second member, namely the body member of the disposable multi-cuvette rotor shown in FIG. 1;

FIG. 5 represents a section through the body member shown in FIG. 4 and along the line shown by the arrows 5—5; and FIG. 5a is an enlarged portion of the body member shown in FIG. 5.

DETAILED DESCRIPTION OF PREFERRED EMBODIMENT

The disposable multi-cuvette rotor 10 of the invention is preferably injection molded of two parts, namely a cover member 12 and a body member 30. Any one of the following group of materials possess the desired transparency, the suitable chemical resistance and absorption characteristics as well as has the necessary optical density to serve as the material from which the rotor 10 may be conveniently injection molded. These materials include the ultraviolet transmitting acrylics, the polyolefins, the styrenes, the polycarbonates, combinations of butadiene and/or acrylonitrile with styrene, the cellulosics, polyamides and the polyester resins. The injection molding of these parts, of course, takes place in suitably formed molds and by means of injection machines, all of which as is well known to those skilled in the art.

The cover member 12 is basically a flat, circular disc having an essentially smooth top side 13 and a bottom side 15 provided with a plurality of ridges 16. These ridges 16 serve for both effecting the joining of the cover 12 and body 30 members to one another as well as sealing off the individual cuvettes, as more fully described below. The cover member 12 is formed with a substantially "D"-shaped central opening 14 and a pair of locating pins 22 protruding from the bottom side 15 (FIG. 3) thereof, the significance of which will be alluded to below. A plurality of ports are provided in the cover member 12 in two concentric rings, namely an outer ring of ports 18 through which reagents may be admitted to the rotor, and an inner concentric ring of ports 20 by means of which samples may be admitted into the rotor. As may be observed, there are always a pair of such ports, namely one reagant loading port 18 and a corresponding sample loading port 20 provided within a particular set so as to be confined by the ridges 16. As may be also observed in FIG. 1 particularly, the diameter of the cover member 12 is greater than that of the diameter of the body member 30, which accounts for the presence of an overhanging flange 24, the significance of which will also be more fully alluded to below.

As may be also observed in particular with reference to FIGS. 1, 2, and 3, there are a plurality of recessed optical windows 26 provided in the top side 13 of the cover member 12 adjacent the flange 24 thereof but always within the ridges 16, substantially as shown. These recessed optical windows must have a surface finish of at least three micro-inches. They are recessed for the purpose of safeguarding their surface finish during handling, lest they become smudged and/or scratched and thus cause errors during absorbance measurements.

The body member 30 is thicker than the cover member 12 and may in general be characterized as possessing a waffle-shaped design. This arises by virtue of the fact that the body member 30 is designed to provide a plurality of individual cuvettes 36 radially arranged like spokes of a wheel in a manner that each of these individual cuvettes 36 is separated from its adjoining cuvette 36 by a series of triangularly-shaped open spaces 48, such as flutes or chutes. The significance of these triangularly-shaped open spaces 48 will be more fully described below.

As may be observed, the body member 30 is also formed with a central, substantially "D"-shaped opening 34 which matches precisely the shape of the central opening 14 of the cover member 12. There is also a pair of locating holes 32 provided in the body member 30 which are designed to cooperate with the pair of protruding locating pins 22 of the cover member 12 so as to facilitate the proper alignment of the two injection molded members to one another prior to their being joined by ultrasonic welding techniques.

Each one of the cuvettes 36 is provided with a means 38 such as a wedge-shaped dam which divides the cuvettes into two adjoining chambers, a reagent/measuring chamber 40 and a sample chamber 42. It should be noted that these adjoining chambers 40 and 42 do communicate with one another through an open space above the dividing means 38. This is so because the dividing means 38 is formed with a height so as to be about one-half of the depth 43 of the cuvette, as may be best observed in FIG. 5a. The wedge-shaped dam 38 is essentially formed of an inclined surface 39 which increases radially outward until it reaches its previously mentioned height and is thereafter formed with an adjoining vertical and slightly arcuate surface 41 leading into the outer reagent/measuring chamber 40. By contrast of course, the inclined surface of the dividing means 38 is contained in the sample chamber 42.

The bottom side of each of the cuvettes 36 is also provided with recessed optical windows 46. These also must possess an optical surface finish of at least three micro-inches. Furthermore, these optical windows 46 are formed in such a manner that when the cover member 12 is aligned and joined to the body member 30, the recessed optical windows 46 of the body member are precisely axially aligned with the recessed optical windows 26 formed in the cover member 12. Thus a representative pair of recessed optical windows 26 and 46 form in effect a pair of opposing planar walls which define an optical path through each of the measuring chambers 40 when the rotor 10 of the invention is used in an absorbance measurement mode within a suitable analytical photometer.

As has already been alluded to above, the disposable rotor 10 of the invention may also be used in a light scattering or fluorescent measuring mode. For this purpose, each of the cuvettes 36 is also provided with an optical end window 44 also provided with an optical surface finish of at least three micro-inches. These optical end windows 44 essentially define the outer radial walls of each of the cuvettes 36, as may be best observed in FIGS. 5 and 5a. Instead of recessing these optical windows, as was the case of the windows 26 and 46, the diameter of the cover member 12 was designed to be larger than the diameter of the body member 30 so that there would be an overhanging flange 24 when the two members 12 and 30 are joined together. This overhanging flange 24 provides the necessary protection to keep the optical surface finishes of the end windows 44 intact during handling since the rotor 10 is being handled by the flange 24.

The rotor 10 of the invention may also be conveniently provided with identifying indicia such as numerals 28 which are designed to be formed on the bottom side 15 of the cover member 12. As may be noted, the rotor 10 of the invention is shown as possessing twenty individual cuvettes 36. Of course, the numbers of these cuvettes may vary, as desired.

After the two parts, namely the cover member 12 and the body member 30, have been injection formed in suitable appropriate molds so as to possess the shapes and characteristics above described, they are aligned to each other by means of the protruding pins 22 and the corresponding locating holes 32, as well as by the respective central and substantially "D"-shaped openings 14 and 34. Thereafter the superimposed two parts are effectively and permanently joined to one another by means of well known ultrasonic welding techniques. During such ultrasonic welding, the ridges 16 function as energy directors and thereby effect not only the joining of members 12 and 30 to one another, but just as importantly, insure cuvette-to-cuvette integrity between adjoining cuvettes 36. This is so since the ridges 16 are formed on the bottom side 15 of the cover member 12 in such a manner as to follow precisely the contour and shape of each of the cuvettes 36 and the ridges 16 completely surround each of such cuvettes 36.

In the now finished rotor 10 of the invention, each cuvette 36 has thus associated therewith one reagent loading port 18, one sample loading port 20 as well as a pair of opposing recessed optical windows 26 and 46 axially aligned through the measuring chamber 40 of each such cuvette. Each of these above-mentioned items are provided within the confines of the ridges 16. In addition, it should be noted that the reagent loading ports 18 are formed in such a manner that when the cover member 12 and body member 30 are joined, these ports 18 are substantially tangentially aligned with the vertical and slightly arcuate surfaces 41 of the divider means 38 so as to admit reagents thereby only into the reagent/measuring chambers 40. It should also be noted that the wedge-shaped dividing means 38 is provided with an inclined surface 39 of such a slant that its projected extension, when cover member 12 and body member 30 are united, would reach the bottom side 15 of the cover member 12 at a point which is radially beyond and outwardly of the reagent loading port 18. This is so as to prevent the samples from being expelled through the reagent loading ports 18 when they are propelled by centrifugal force over these dividing means 38 so as to be mixed with the reagents in the reagent/measuring chambers 40.

The significance of the triangularly-shaped open spaces 48, which give the rotor 10 a generally waffle-shaped appearance, resides in that it permits a more rapid incubation and temperature equilibration to be achieved not only throughout the entire rotor 10, but also within each and every one of the radially arranged cuvettes 36 and its contents. Such enhanced incubation and equilibration time is facilitated when the corresponding support of the analytical photometer is provided with a support member formed with protruding triangularly-shaped projections to fit into these triangularly-shaped open spaces 48, especially if such projections also contain suitable heaters. The significance of temperature, its equilibrium both within each cuvette and throughout the rotor, is more fully described in an article entitled "A Propagation of Error Analysis of the Enzyme Activity Expression. A Model for Determining the Total System Random Error of a Kinetic Enzyme Analyzer," *Clinical Chemistry*, Vol. 22, No. 9, 1976, on page 1445 thereof.

Although the invention has been described above in connection with a preferred embodiment thereof, it is clear that certain modifications are possible with respect to particular applications of the invention so that the preferred embodiment thereof shown in the drawings and described above is to be understood as being only by way of example.

What is claimed is:

1. A disposable multi-cuvette rotor for use in an analytical photometer comprising a one piece body member of injection molded transparent material that has a planar upper surface and defines a circumferential array of spaced, elongated, radially extending recesses, said planar upper surface defining the upper edge of each of said recess, each said recess defining a first chamber and a second chamber disposed radially outward from said first chamber, and separator structure integral with said body member between said first and second chambers, said separator structure including a ramp surface that is inclined with respect to said planar upper surface and that forms the radial outer boundary of said first chamber and a vertical surface that extends perpendicularly to said planar upper surface and that forms the radial inner boundary of said second chamber, a first optical window integral with said body member in the bottom wall of said second chamber, and a further integral optical window in the radial outer wall of said second chamber, the inner surface of each said further optical windows extending perpindicular to said planar upper surface the upper surfaces of all of said optical windows being parallel to and spaced the same predetermined distance below said planar upper surfaces; and a one piece cover member of injection molded transparent material that has a planar lower surface parallel to and immediately adjacent said planar upper surface of said body member with a continuous seal extending around each said recess between said upper and lower surfaces to define an analytical cuvette, a first circumferential array of ports in said cover member aligned with corresponding first chambers of said circumferential array of recesses in said body member, a second circumferential array of ports in said cover member disposed radially outward from said first array of ports and aligned with corresponding second chambers of said circumferential array of recesses in said body member, and a circumferential array of second optical windows integral with said cover member and disposed radially outward from said second array of ports and aligned with corresponding first optical windows, the lower surface of each said second optical windows being parallel to said planar lower surface of said cover member such that each pair of opposed aligned surfaces of corresponding first and second optical windows are parallel and define an optical path of precise and stable path length, the lengths of said optical paths in all of said second chambers being the same.

2. The disposable multi-cuvette rotor of claim 1 in which said rotor is made of acrylic resin.

3. The disposable multi-cuvette rotor of claim 1 wherein each of said first and second optical windows is recessed and has an optical surface finish of at least three micro inches quality.

4. The disposable multi-cuvette rotor of claim 1 wherein the diameter of said cover member is greater than the diameter of said body member such that an overhanging flange is provided that protects the optical surface finishes of said further windows.

5. The disposable multi-cuvette rotor of claim 1 wherein said body member includes triangularly-shaped open spaces that separate adjacent radially extending rectangularly-shaped recesses.

6. The disposable multi-cuvette rotor of claim 1 or 36 wherein said rotor has a substantially D-shaped, central opening whereby said rotor may be securely located with respect to a correspondingly shaped support.

7. The disposable multi-cuvette rotor of claim 1 wherein said cover and body members include ultrasonic welded bonds that join said cover and body members together and form said continuous seals that define said analytical cuvettes.

8. The disposable multi-cuvette rotor of claim 1, 3, or 4 wherein said body member and said cover member are made of transparent material of suitable chemical and absorption characteristics selected from the group of acrylics, polyolefins, styrenes, polycarbonates, combinations of butadienes and/or acrylonitrile with styrene, cellulosics, polyamides, and polyesters.

* * * * *

UNITED STATES PATENT AND TRADEMARK OFFICE
CERTIFICATE OF CORRECTION

PATENT NO. : 4,226,531
DATED : October 7, 1980
INVENTOR(S) : Thomas O. Tiffany, et al.

It is certified that error appears in the above—identified patent and that said Letters Patent are hereby corrected as shown below:

Column 7, line 16, "said optical" should be --said first optical--.

Column 7, line 18, "surfaces" should be --surface--.

Column 8, line 24, "claim 1 or 36" should be --claim 1 or 3--.

Signed and Sealed this

Tenth Day of February 1981

[SEAL]

Attest:

RENE D. TEGTMEYER

Attesting Officer    Acting Commissioner of Patents and Trademarks